United States Patent [19]

Horowitz et al.

[11] Patent Number: 5,599,891

[45] Date of Patent: Feb. 4, 1997

[54] POLYMER COMPOSITION

[75] Inventors: Daniel M. Horowitz, Washington, D.C.; Brian K. Hunter, Kingston, Canada; Jeremy K. M. Sanders, Cambridge, United Kingdom; Joachim Clauss, Mühltal, Germany; Neil George, Stocton on Tees, United Kingdom

[73] Assignee: Zeneca Limited, London, England

[21] Appl. No.: 407,030

[22] PCT Filed: Sep. 28, 1993

[86] PCT No.: PCT/GB93/02014

§ 371 Date: Aug. 8, 1995

§ 102(e) Date: Aug. 8, 1995

[87] PCT Pub. No.: WO94/07940

PCT Pub. Date: Apr. 14, 1994

[30] Foreign Application Priority Data

Sep. 28, 1992 [GB] United Kingdom ............... 9220401
Sep. 28, 1992 [GB] United Kingdom ............... 9229447
Mar. 8, 1993 [GB] United Kingdom ............... 9304651

[51] Int. Cl.$^6$ ..................................................... C09J 3/12
[52] U.S. Cl. ........................ 527/202; 528/361; 527/200; 527/202

[58] Field of Search ....................... 528/361; 527/200, 527/202

[56] References Cited

FOREIGN PATENT DOCUMENTS

| 145233 | 6/1985 | European Pat. Off. . |
| 535534 | 4/1993 | European Pat. Off. . |
| 2108074 | 5/1983 | United Kingdom . |

OTHER PUBLICATIONS

Koosha et al: "The Surface and Chemical Structure of Poly(beta–hydroxybutarate) Macroparticles Produced by Solvent Evaporation Process", Journal of Controlled Release, vol. 9, No. 2, 1989, pp. 149–157.

Patent Abstracts of Japan, vol. 014, No. 310, (C–0736) Jul. 4, 1990, & JP,A,02 105 826, see abstract.

Primary Examiner—Samuel A. Acquah
Attorney, Agent, or Firm—Cushman Darby & Cushman IP Group Pillsbury Madison & Sutro LLP

[57] ABSTRACT

A polymer composition comprising a crystallisable polymer stabilised in an amorphous or incompletely crystalline state by forming particles at least partly coated with a surfactant or phospholipid and to processes for preparing a such a polymer composition.

11 Claims, No Drawings

POLYMER COMPOSITION

This application is a 371 of PCT/GB93/02014 filed Sep. 28, 1993.

This invention relates to a polymer composition and in particular to a crystallisable polymer stabilised in an amorphous or incompletely crystalline state and to processes for preparing a such a polymer composition.

In processing a crystallisable polymer it is sometimes desirable to hold it in an amorphous or incompletely crystalline state while particular operations are carried out. Whereas this can be done by melting the polymer and chilling it, or having plasticiser present, or using it as a solution, it would be convenient if the polymer could be amorphous or incompletely crystalline when stored and at the start, or possibly even at the end, of processing.

It has been suggested (Sanders et al. International Symposium on bacterial polyhydroxyalkanoates, University of Göttingen, 1–5 Jun. 1992; de Koning et al. Polymer Communications 1992, 33 (15), 3292–3294) that one such polymer, polyhydroxybutyrate (PHB), when in the form of the microscopic particles in which it is produced in certain microorganism cells, is amorphous and remains amorphous for long periods, because of the rarity of homogeneous nucleation events in discrete single particles and the mutual isolation of the particles. A possible explanation for this behaviour is that native granules or particles are very small, reaching a maximum diameter of about 0.25 μm in *Alcaligenes eutrophus* or 0.7 μm in *Bacillus megaterium*. The expected frequency of homogeneous nucleation within a given granule (f) is very low, on the order of $10^{-8}$ events/second or less. Under the most conservative set of assumptions (granule diameter of 1 μm, nucleation rate of 30 events $mm^{-3}sec^{-1}$), the predicted half-life of amorphous, granular PHB is $4.4\times10^7$ seconds, or 510 days. Using more realistic assumptions (granule diameter 0.25 μm, nucleation rate at 30° C. of 2.5 events $mm^{-3}sec^{-1}$), the predicted half life is some $3.4\times10^{10}$ seconds, in excess of 1000 years. By contrast, when the polymer is harvested from the cell, the natural particle coatings are removed, the particles are allowed to collide and possibly coalesce which opens the possibility for heterogenous nucleation or more frequent homogeneous nucleation to occur and rapid crystallisation ensues. Thus a bulk sample of PHB crystallises rapidly to an extent of 50% or more, at ambient temperature, usually in less than an hour.

It is desirable in certain circumstances to be able to maintain the amorphous nature of the polymer for a significant period of time after the polymer is prepared or harvested. Similarly, it may be desirable to rejuvenate crystallised polymer and maintain it in the amorphous or incompletely crystalline state until ready to be used. The applicants have found that it is possible to maintain the amorphous or incompletely crystalline state of the polymer for significant periods of time if the polymer is maintained in the form of small particles each particle with a coating of surfactant or phospholipid.

Thus, according to the present invention there is provided a polymer composition substantially free of cellular protein comprising a crystallisable polymer in the form of particles having a largest dimension in the range of 0.1 to 5 μm and having on their surface a surfactant other than a sugar-based surfactant having a molecular weight less than 2000 other than a sugar-based surfactant having a molecular weight less than 2000 or a phospholipid, said polymer having a molecular weight $M_w$ of over 50000 and having a crystallisation half life of more than 0.1 day at ambient temperature.

The polymer is especially one which is capable of a relatively high level of crystallinity, for example over 30%, especially 50–90%. Such polymers may be biologically or synthetically produced.

Suitable biologically produced polymers typically include at least one biologically produced polyhydroxyalkanoate (PHA) having units of formula I:

$$-O-C_mH_n-CO- \qquad (I)$$

where m is in the range 1–13 and n is 2m or (when m is at least 2) 2m–2. Typically $C_mH_n$ contains 2–5 carbon atoms in the polymer chain and the remainder (if any) in a side chain. In very suitable polyesters m is 3 or 4, n is 2m and especially there are units with m=3 and m=4 copolymerised together with respectively a $C_1$ and $C_2$ side chain on the carbon next to oxygen. Particular polyesters contain a preponderance of m=3 units, especially with at least 70 mol % of such units, the balance being units in which m=4. The molecular weight of the polymer is especially over 100000, up to eg $2\times10^8$.

Polyester of formula (I) containing only m=3 units is PHB, polyester containing m=3 and m=4 units is the copolymer of polyhydroxy-butyrate-covalerate (PHBV). PHBV preferably contains 4–20% of m=4 units. The polyester can also be a blend of two or more PHAs differing in the value of m. A particular example contains:
(a) polymer consisting essentially of Formula I units in which 2–5 mol % of units have m=4, the rest m=3; and
(b) polymer consisting essentially of Formula I units in which 5–30 mol % of units have m=4, the rest m=3.

The proportions of the polymers in such a blend are preferably such as give an average m=4 content in the range 4–20 mol %.

The polyhydroxyalkanoate can be a fermentation product, especially of a microbiological process in which a microorganism lays down polyhydroxyalkanoate during normal growth or is caused to do so by cultivation in the absence of one or more nutrients necessary for cell multiplication. The microorganism may be wild or mutated or may have had the necessary genetic material introduced into it, Alternatively the necessary genetic material may be harboured by a eukariote, to effect the microbiological process.

Examples of suitable microbiological processes are the following: for Formula I material with m=3 or m=partly 3, partly 4: EP-A-69497 (*Alcaligenes eutrophus*); for Formula I materials with m=3: U.S. Pat. No. 4,101,533 (*A. eutrophus*), EP-A-144017 (*A. latus*); for Formula I material with m=7–13: EP-A-0392687 (various Pseudomonas).

In such processes the polymer can be extracted from the fermentation product cells by means of an organic solvent, or the cellular protein material may be decomposed using an aqueous route leaving microscopic particles of polymer. For specialised end uses the cellular protein may be partly or wholly allowed to remain with the polymer, but preferably subjected to cell breakage. A useful process for extraction is given in EP-0 145 233.

Alternately the PHA may be synthesised by chemical processes known in the art. PHB can be prepared according to Bloembergen, S. and Holden, D. A., Macromolecules. 1989, Vol 22, p 1656–1663. PHBV can be prepared according to Bloembergen, Holden, Bluhm, Hamer and Marchessault, Macromolecules. 1989, Vol 22, p 1663–1669.

The invention is applicable also to synthetic polymers which are capable of crystallisation, especially:
a polyester, for example head-to-tail polyester or (preferably) substantially stoichiometric head-to-head tail-to-tail polyester;
b polyester having only alcohol or phenol reactivity or only acyl reactivity;

c other polymers, such a polyamides, having potential acylatable and or esterifiable groups.

Such polymers may be used alone, in combination or with one or more microbiologically derived polymers as described above. Examples of suitable synthetic polymers are synthetic polyesters, especially polycaprolactone, polylactides, and polymers such as those described in PCT application WO 92/09654, particularly such polyesters containing combinations of dicarboxylic acids or derivatives thereof and diols. Dicarboxylic acids being selected from the group consisting of malonic, succinic, glutaric, adipic, pimelic, azelaic, sebacic, fumaric, 2,2-dimethylglutaric, suberic, 1,3-cyclopentane dicarboxylic, 1,4-dicyclohexane-dicarboxylic, 1,3-cyclohexane dicarboxylic, diglycolic, itaconic, maleic, 2,5-norbornane dicarboxylic, 1,4-terephthalic, 1,3 terephthalic and ester forming derivatives thereof and combinations thereof, and diols selected from the group consisting of ethylene glycol, diethylene glycol, proplyene glycol, 1,3-propanediol, 2,2-dimethyl-1,3-propanediol, 1,3 butanediol, 1,4-butanediol, 1,5-pentanediol, 1,6-hexanediol, 2,2,-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethyleneglycol, tetraethyleneglycol, di-, tri-, tetra-proplyeneglycol and combinations thereof.

Other crystallisable polymers which may be mentioned, either alone or in combination with any of the polymers mentioned herein are polyethylene, polypropylene, polybutene, polystyrene, poly(chlorotrifluoroethylene), polyoxymethylene, poly(ethylene oxide), poly(tetramethylene oxide), poly(propylene oxide), poly(deamethylene sebacate), poly(decamethylene terephthalate), nylon, p-ethylene, p-(propene), p-(1-butene), p-(styrene), p-(chlorotrifluoroethylene), p-(isoprene), p-(methylene oxide), p-(ethylene oxide), p-(propylene oxide), polycarbonate, polyvinylalcohol, cellulose and cellulose acetates or butyrates, polypeptides and proteins, polymethylmethacrylate.

Preferred polymer compositions are biodegradable or contain at least one biodegradable polymer and are capable of at least partial biodegradation.

In or with the polymer there may be other materials (i.e. additives) present provided they do not promote crystallisation and thereby reduce the crystallisation half life of the particulate polymer to less than 0.1 day at room temperature. In particular one or more plasticisers may be present. The ratio of plasticiser to polymer depends on the intended use of the composition. The range 2–40 phr w/w includes most of the likely uses. For making effectively rigid but not brittle articles the range 5–20 especially 6–12, phr w/w is generally suitable.

Any of the known plasticisers for these polymers are suitable and any plasticisers which are found to plasticise these polymers subsequent to this invention would be suitable for use herein. Examples of suitable plasticisers are:
(a) high boiling esters of polybasic acids, such as phthalates, isophthalates, citrates, fumarates, glutaate, phosphates or phosphites. The esterified radicals may be for example $C_1$–$C_{12}$ alkyl, aryl or aralkyl. Particular examples are dioctyl-, dieptyl- and decyl-phthalates and dialkylalkylene oxide glutaate (Pasthall 7050);
(b) high boiling esters and part of polyhydric alcohols, especially glycols, polyglycols and glycerol. The acid derived radicals of the ester typically contains 2–10 carbon atoms. Examples are triacetin, diacetin and glyceryl dibenzoate;
(c) aromatic sulphonamides such as paratoluene sulphonamide.

A particularly preferred plasticiser is a doubly esterified hydroxycarboxylic acid having at least 3 ester groups in its molecule. "Doubly esterified" means that at least some of the hydroxy groups of the hydroxycarboxylic acid are esterified with a carboxyiic acid and at least some of the carboxy groups thereof are esterified with an alcohol or phenol. Preferably at least the hydroxycarboxyiic acid from which the ester is derived is aliphatic or cycloaliphatic. Its backbone structure (that is, apart from carboxy groups) preferably contains 2–6 carbon atoms. It contains preferably 2–4 carboxy groups and 1—3 hydroxy groups; and preferably the number of carboxy groups exceeds the number of hydroxy groups. An example of such a plasticiser is Estaflex* (acetyltri-n-butyl citrate). (* indicates a Trade Mark).

The polymer composition may contain any other of the additives commonly used in polymer processing, for example, pigment, particulate or fibrous or platy filler or reinforcer, and nucleating agents, especially boron nitride, talc, ammonium chloride or DZB/Zn Stearate.

If a nucleating agent is present, it is preferably in amounts in the range from 0.2 to 2 phr.

In the present invention, small particles of PHAs are preferably from 0.1 to 3 μm, especially 0.1 to 2.0 μm.

The size range for a technically convenient crystallisation half life differs among polymers. In the microbiologically produced polyesters defined above, the higher value of m, the larger the particle sizes can be, since such polyesters crystallise more slowly. It is practicable to choose a particle size range to suit the crystallisation half life defined for a particular end use of the polymer.

The crystallisation half life of the particulate polymer at ambient temperature is at least 0.1 day, particularly at least 1 day, preferably at least 1 week (7 days), especially 6 months (168 days) or more.

During storage they should not be exposed to agencies that would promote crystallisation, such as atmospheric impurities or radiations.

The particles can be of any shape, but preferably are approximately spherical with an aspect ratio of up to 2 to avoid accidental fracture leading to nucleation events.

If the polymer is microbiologically produced, it should be sufficiently free of cell material to permit the surfactant access to the surface of the particles. If any cell wall material is present, it may be at least partly broken.

The surfactant or phospholipid should form a close-packed absorbed layer over at least 50% of the surface of the particles. Preferably, it covers at least 80% of the surface and most desirably it forms a complete layer.

The surfactant or phospholipid coated particles can be prepared by taking incompletely or wholly crystallised polymer and dissolving the polymer in a solvent which recovers the amorphous nature of the polymer and then forming the coated particles by emulsification with a surfactant or phospholipid.

Thus, the invention in a second aspect provides a process of making the polymer composition by the steps of:
(a) dissolving the polymer in a solvent of low solubility in water;
(b) emulsifying the resulting solution in an aqueous solution of a surfactant or phospholipid; and
(c) removing solvent from the resulting emulsion disperse phase.

The surfactant can be anionic, cationic, non-ionic, zwitterionic or contain hydrophilic groups of more than one type. Very suitably it is cationic or anionic and preferably its hydrophilic part is quaternary ammonium, for example tri $C_1$–$C_4$ alkylammonium. The hydrophobic part of the surfactant preferably contains at least 8, especially 12–20, carbon atoms. Alternately the surfactant may be an ethoxylate, for example, an alkyl ethoxylate containing 7 to 16 carbons and up to 100 ethoxylate units, or a block copolymer of ethylene oxide and propylene oxide or a nonylphenylethoxylate. Very suitably, the surfactant contains a linear alkyl group especially when the polymer is biodegradable. Suitable surfactants include: dodecyl-trimethylammonium bromide, tetradecyltrimethylammonium bromide, cetyltrimethylammonium bromide, cetyldimethyl-ethylammonium bromide, benzyldimethyldodecylammonium bromide, benzyldimethyltetradecylammonium bromide, benzyldimethylhexadecylammonium bromide, benzalkonium chloride, benzethonium chloride, methylbenzethonium chloride, cetylpyridinium chloride, sodium dodecyl sulphate, sodium Sarkosyl*, sodium dioctylsulfosuccinate, sodium cholate, sodium deoxycholate, sodium laurate, sodium myristate, sodium palmitate, sodium stearate, sorbitan monopalmitate. Of this group of surfactants the preferred are cetyltrimethylammonium bromide, sodium deoxycholate, sodium dodecyl sulphate, sodium Sarkosyl and sodium dioctylsulfosuccinate. (Sarkosyl is a proprietary name).

The phospholipid is suitably a natural occurring or artificial phospholipid. The phospholipid may be selected from the following group: phosphatidylcholine (e.g. soy phosphatidyl-choline), phosphatidyl-ethanolamine, phosphatidylglycerol, di-phosphatidyl glycerol, phosphatidyl-serine, phosphatidyl-threonine, phosphatidyl-inisotol, phosphotidyl-glycerol phosphate, phosphatidyl-(n-methyl) ethanolamine, phosphatidyl-(n-dimethyl) ethanolamine, phosphatidic acid, phosphatidyl-(myo)inisotol, phosphatidyl-(myo)inisotol-4-phosphate, phosphatidyl-(myo)inisotol-4,5-phosphate, phosphatidyl-(myo)inisotol dimmoside, o-amino-acid ester of phosphatidal glycerol and phosphoglycerides.

The content of surfactant or phospholipid is at least sufficient to form a close-packed absorbed layer of the surfactant or phospholipid over at least half the surface of the particles. Preferably it is sufficient to form a complete layer, and an excess of e.g. up to 100% may be present. However, it is preferred to minimise the content of surfactant, since it may be an undesired impurity in some subsequent uses of the polymer.

Emulsification of the polymer solution can be carried out by any suitable means, for example, by mechanical agitation or sonication. High pressure homogenisation is useful for controlling the size of the particulate polymer.

When the solvent is substantially insoluble in water it appears that ease of removal of the solvent depends on its vapour pressure: thus it preferably has a boiling point not over 120° C., preferably not over 85° C. Suitable solvents for PHAs are hydrocarbons and halogenated hydrocarbons, for example, chloroform, methylene chloride or 1,2-dichloroethane. The suitable solvents depend on the particular polymer system. When the polymer is a microbiological polyester the solvent is preferably chloroform or methylene chloride. Operational arrangement should include precautions for safe handling of such solvents and compositions containing them.

The concentration of polymer in the solvent may be chosen to suit the polymer particle size required after removal of the solvent. The polymer particle size can also be controlled by control of the particle size of the emulsion disperse phase. The surfactant is preferably as defined above. Its concentration is suitably in the range 1–100, especially 2–50 mM.

Removal of solvent from the emulsion may be by any suitable means, heating the emulsion, for example to 70° C. in air, bubbling gas through the emulsion, for example nitrogen gas, rotary evaporation of the emulsion, or simply removing solvent by room temperature evaporation from a large surface area, for example for 24 hours. Such an operation which involves heating the polymer is preferably carried out at subatmospheric pressure, to avoid temperatures at which crystallisation of the polymer is more rapid. If the solvent and water do not differ much in volatility, make-up water may be fed to the emulsion to prevent an undue rise in concentration. If the volatilities are suitably balanced, the whole emulsion can be air-dried to give flowable dry polymer particles.

An alternative means of solvent removal is by dialysis through a membrane permeable to the solvent but not dissolved or swollen by it. A suitable membrane is made of cellulose; other hydrophilic or water-wettable membrane materials can be used. On the side of the membrane ("external") away from the emulsion ("internal") there may be any convenient fluid medium in which fugacity of the solvent is less. Thus the fluid may be a gas, for example air, or an organic liquid in which the solvent is soluble. A very suitable fluid is an aqueous solution containing a surfactant and capable of emulsifying the solvent.

It appears that this process is operative because the compound, although of limited solubility in water, is soluble in the hydrophobic domains of the micelles of the amphipathic agent. The concentration of that agent should be at least its critical micelle concentration or should attain that concentration on receiving some of the compound.

The amphipathic agent should have a moderate to high hydrolyophilic balance (HLB), so that water forms the continuous phase of the aqueous solution. It is, however, within the scope of the invention to use a relatively low HLB, such that with continuing absorption of the compound the emulsion undergoes inversion to water-in-oil.

Suitable amphipathic agent suffactants are, for example, emulsifiers, dispersing agents, detergents and wetting agents. Others not especially valuable for those duties may be suitable for the process. The hydrophilic part of the agent can be anionic, cationic or non-ionic or contain more than one such function. The hydrophobic part can be aliphatic, aromatic or polymeric or of more than one such type. It preferably is a group that, in absence of the hydrophilic part, would have a melting point under 100° C., especially under 50°, so as to assure ready solubility of the compound in its micelles. Very suitably the surfactant is cationic and preferably its hydrophilic part is quaternary ammonium, for example tri $C_1$–$C_4$ alkylammonium. The hydrophobic part of the surfactant preferably contains at least 8, especially 12–20, carbon atoms. Very suitably it is a linear alkyl group.

The concentration of hydrophobic, that is, dissolving, material in the aqueous solution may be enhanced by having present a non-volatile liquid emulsified in the micelles.

The amphipathic agent should have a low or zero tendency to foam. If desired an anti-foaming agent such as a silicone or a $C_4$–$C_{12}$ alcohol may be present.

Contact of the fluid phase with the aqueous solution may be effected by any conventional means, for example spray towers containing plates or random packing, falling film contactors or wiped surface contactors, when that fluid is a gas. When that fluid is a gas, and more especially when it is a liquid, contact may be through a membrane.

In the preferred process of contact through a membrane the fluid phase preferably is emulsion of the compound in an aqueous solution of at least one amphipathic agent. The amphipathic agents on the two sides of the membrane should not of course mutually interact undesirably: thus in general it is not desirable to have a cationic on one side and an anionic on the other. The emulsion disperse phase may initially be a solution of a species, such as a polymer, incapable of permeation through the membrane as described in Example 1.

The membrane should be hydrophilic or water-wettable. Suitably it is made of cellulose and may have a molecular weight cutoff in the range 10000–20000 Da.

Since in such a system the compound can pass in either direction and, indeed, one could pass in one direction and another in the other direction according to the chemical potential of the respective species involved, the invention in a second aspect provides a process of transferring a compound of limited solubility in water from one aqueous amphipathic solution to another through a membrane permeable to said compound.

The process is especially applicable to volatile compounds, preferably boiling at not over 120, especially not over 85° C. at atmospheric pressure, for example hydrocarbons and halogenated hydrocarbons.

The external surfactant should be incapable of interfering reactions with the internal surfactant. For example it should not be anionic if the internal surfactant is cationic. The external surfactant is preferably at above its critical micelle concentration. It may contain an emulsified low-volatility liquid in which the solvent is soluble. When the external fluid is a liquid the solvent of the emulsified polymer solution can be relatively non-volatile since the external fluid can provide enough diluting capacity.

Operating conditions for removal of solvent through a membrane are chosen to suit requirements of selectivity and speed. In one preferred set of conditions the membrane has a molecular weight cut off of 10000–20000 Da (which would permit passage of surfactant) and the external fluid has the same surfactant concentration as the internal. Analogously the surfactant concentration in the polymer latex may be increased or decreased. Using a membrane having a lower molecular weight cutoff there is less need to equalise the external and internal surfactant concentrations.

In a further method of solvent removal, a further liquid, chosen to reverse the partition of the solvent between the emulsion disperse phase and continuous phase, is added.

Preferably the process is carried out at temperatures in the range 10°–50° C.

An alternative process for the preparation of a polymer composition comprising surfactant or phospholipid coated small particles (also referred to herein as particulate polymer) of polymer, is to form the particles during the harvesting stage of a microbiological production process. If the polymer is microbiologically produced polyester laid down in organism cells the particulate polymer may be made by at least partly replacing cell material by the surfactant. This may be done at any convenient stage during recovery of polyester particles from cells, provided the polyester is incompletely crystalline.

The particulate polymer can be made during the bulk preparation processes known for PHAs. EP-A 0 145 233 discloses a process in which an aqueous suspension of micro-organism cells containing a PHB polymer are subjected to a proteolytic enzyme digestion and/or a surfactant digestion in order to solubilise non-polymer cell material. Prior to, or during the digestion, but before any proteolytic enzyme digestion step, the suspension is heated to at least 80° C. to denature nucleic acids which otherwise hinder separation of the PHB containing residue from the suspension. In a preferred aspect of this process, after solubilisation of the non-polymer cell material, the residual material is treated with hydrogen peroxide. If the cells are subjected to a surfactant digestion, the surfactant is removed prior to the hydrogen peroxide treatment. The disclosure of EP-A 0 145 233 is incorporated herein.

In the processes of the present invention addition of the surfactant during the hydrogen peroxide step of the bulk process gives a latex of surfactant coated small particles. If desired an anti-foaming agent such as a silicone or a $C_4$–$C_{12}$ alcohol may be present.

Thus according to a further aspect of the present invention there is provided a process for the preparation of polymer composition comprising a crystallisable polymer in the form of small particles, each particle being at least partly coated with a surfactant or phospholipid comprising lysing microorganism cells containing crystallisable polymer and removing non-polymer cell material from the surface of the polymer using an oxidising agent in the presence of a surfactant or phospholipid.

The oxidising agent can be any oxidising agent capable of removing or solubilising non-polymer cell material. Preferably the oxidising agent is a peroxide, for example, hydrogen peroxide.

The result of this preparation method is a latex which can be used to store the particulate polymer in the amorphous or incompletely crystalline state, for at least 0.1 day, preferably 1 day, especially 1 week and particularly for 6 months or more.

Alternately the latex can be spray-dried in the usual way.

When the particulate polymer prepared by any of the processes is subjected to a drying process such as spray-drying or air-drying, the surfactant coating may be disrupted and crystallisation of the polymer may start. However a further advantage of the particulate polymer of the invention is that the rate of crystallisation of the coated particles is significantly slowed compared to polymer produced by the usual methods. This is particularly useful for polymers which normally develop high levels of crystallinity quickly after preparation. Such particles being incompletely crystalline and being at least partly coated with a surfactant or phospholipid fall within the scope of the present invention if the crystallisation half life is greater than 0.1 day at ambient temperature.

Using this preparation method to prepare spray-dried particles of polymer has the further advantage that in the bulk preparation of polymer, the surfactant coating stops flocculation of the small particles, providing a suspension rheology which particularly aids centrifugation on the plant. However, the latex can be stored in this form and spray-dried at any time convenient to the operator.

The surfactant for use in preparing an aqueous latex of surfactant coated particles in bulk preparation processes can be any of the previously mentioned surfactants or phospholipids. The surfactant is preferably a non-ionic surfactant and is preferably chosen from the group comprising alkylethoxylates, preferably containing 9 to 20 carbons in the alkyl group, especially 16 carbon atoms, and between 7 and 100, preferably 20 ethoxylate units; aromatic ethoxylates, for example nonylphenylethoxylate; block copolymers of ethylene and propylene oxide having the general formula H—(OCH$_2$CH$_2$)$_a$—(OCH(CH$_3$)—CH$_2$)—(OCH$_2$CH$_2$)$_a$—OH.

Whichever process is used for producing the particles, any crystalline particles produced, intentionally or not, can be separated from amorphous or incompletely crystalline particles by mild centrifugation, eg at 1000–5000 g. Thereafter, if desired, the amorphous or incompletely crystalline particles (which are of lower density than such crystalline particles) can be concentrated or separated by stronger centrifugation, eg at 5000–100000 g.

Thus, the polymer in the form of small particles can be prepared as a flowable powder of individual particles or loose agglomerates. Such agglomerates preferably have limited cohesion to prevent nucleation events being transmitted between particles within them, or are small enough to limit bulk crystallisation.

Since production of such powder requires special care to avoid nucleation events and consequent crystallisation, the particulate polymer is preferably prepared in the form of a dispersion in a liquid in which the polymer is substantially insoluble.

Thus, as a preferred aspect of the invention, there is provided an aqueous latex of the polymer, preferably containing 1–50, especially 5–20, weight percent of polymer.

The particulate polymer can be used in any of the usual methods for forming shaped articles such as injection moulding, compression moulding, extrusion of fibre or films, extrusion of profile, gas-current spinning, tack spinning, coating melt onto substrate, coating latex onto substrate, shaping solution in volatile solvent. In such processes the particulate polymer is effectively confined and coalesces to form a polymer structure, i.e. a shaped article.

Examples of articles made by such methods include films especially for packaging, coated products (such as paper, paperboard, non-woven fabrics), fibres, non-woven fabrics, extruded nets, personal hygiene products, bottles and drinking vessels, agricultural and horticultural films and vessels, sustained or controlled-release granules devices, ostomy bags. Alternatively, the particulate polymer can be used as an adhesive.

Thus, the invention in a further aspect provides a process of making a polymer structure by confining polymer particles according to the first aspect and, as appropriate, causing mutual adhesion and/or crystallisation thereof.

The particles can if desired contain a solvent for the polymer and, if made by the processes of the second aspect of the invention, can be applied as the emulsion formed in step (b), possibly with incomplete solvent removal in step (c). By this means the number of processing steps is decreased.

A particular preferred example of a process comprises coating an aqueous latex of such polymer particles over a solid surface, then causing mutual adhesion and crystallisation possibly with adhesion to that surface. Very conveniently this process uses the polymer particles in latex form. The solid surface is especially a woven or non-woven fabric, especially paper or paper board.

In a further embodiment of the invention, one or more active ingredient(s), for example, a pharmaceutical or an agrochemical could be incorporated into the small particles of the polymer during production. The particulate polymer containing such active ingredient could be used to form controlled or sustained release granules or devices, or could be used directly by injection or ingestion of aqueous suspensions, or by superficial coatings of aqueous suspensions.

EXAMPLE 1

Preparation of Amorphous PHB Particles

Poly(R-3-hydroxybutyrate) homopolymer (PHB) (formula I, $C_mH_n$=—CH(CH$_3$)CH$_2$— of $M_w$ 666000 and $M_n$ 206000 (by GPC), as obtained from *Alcaligenes eutrophus* cells by enzymatic decomposition of cell material followed by spray drying, melting and quenching, was dissolved at 5% w/v in chloroform. The solution was sonicated at 20 kHz in 20 volumes of cetyltrimethylammonium bromide (CTAB) solution at various concentrations in the range 1 to 50 mM at 20° C. for up to 20 min. The emulsion obtained in 5 mM CTAB was dialysed against 3 changes of aqueous CTAB (5 mM) for 24–48 h using a tubular cellulose membrane having a molecular weight cutoff of 12000–14000 Da. At the end of this time the polymer remained dispersed in the solution in the form of a latex of extremely fine partly translucent particles that showed no tendency to coagulate. The particles were visible in the transmission electron microscope as non-birefringent 0.1 to 0.3 micron diameter approximate spheres.

A sample of the dispersed polymer was separated by two 30 minute rounds of centrifugation at 8000 g and 33,0000 g respectively. The amorphous particles were resuspended in D$_2$O and examined by solution-state $^{13}$C—NMR spectroscopy (see note below). The particles showed sharp spectral lines at temperatures in the range 50°–90° C., but no trace of chloroform. Control samples of crystalline polymer and of polymer cooled rapidly from the melt gave no signal. The NMR spectrum of the prepared particles was identical with that of the polymer particles in whole cells. The spectra show the polymer to be highly amorphous with the signal intensities comparable to those seen for polymer particles in whole cells.

Sucrose density columns were used to estimate the relative density of the particles. The theoretical density of amorphous PHB is 1.176. The crystalline PHB control starting material had a density of 1.25. The prepared particles were of density 1.15–1.18. Predominantly the particles appeared,to be amorphous. NOTE: In this high resolution solution-type $^{13}$C NMR spectroscopy relatively sharp PHB resonances depend on the presence of local molecular motions at frequencies of the order of $10^7$ s$^{-1}$. These motions are present in elastomers but not in crystalline or amorphous immobile solids. Thus PHB immobile solid shows no PHB resonances. A mixture of elastomer and such solid would show some loss of intensity but no change of apparent line width. A general but partial loss of molecular mobility would show line broadening but no loss of intensity.

The method of Example 1 was repeated using the solvents listed in Table 1 below. The crystalline content of the particles are given as + or ++, where + means less than 40% crystalline and ++ means less than 10% crystalline. (Hereinafter proprietary names are indicated by an asterisk *).

TABLE 1

| | | |
|---|---|---|
| Dodecyltrimethylammonium Br | 5/50 mM | + |
| Tetradecyltrimethylammonium Br | 5/50 mM | ++ |
| Cetyltrimethylammonium Br | 1–100 mM | ++ |
| Cetyldimethylethylammonium Br | 50 mM | ++ |
| Benzyldimethyldodecylammonium Br | 50 mM | + |
| Benzyldimethyltetradecylammonium Br | 50 mM | + |
| Benzyldimethylhexadecylammonium Br | 50 mM | ++ |
| Benzalkonium Cl (C8 to C18) | 5/50 mM | ++ |
| Benzethonium Cl | 5/50 mM | ++ |
| Methylbenzethonium Cl | 5/50 mM | ++ |
| Cetylpyridinium Cl | 5/50 mM | ++ |
| Sodium dodecyl sulphate | 50 mM | ++ |
| Sodium Sarkosyl* | 50 mM | ++ |
| Sodium Dioctylsulphosuccinate | 25 mM | ++ |
| Sodium Deoxycholate | 50 mM | +++ |
| Sodium Cholate | 50 mM | ++ |
| Sodium Laurate | 50 mM | ++ |
| Sodium Myristate | 10 mM[a] | ++ |
| Sodium Palmitate | 5 mM[a] | ++ |
| Sodium Stearate | 5 mM[a] | + |
| Sorbitan Monopalmitate | 2% (w/v)[ab] | + |

[a]limited water solubility
[b]surfactant was dissolved in the organic phase at the concentration inidicated.

EXAMPLE 2

Granule Stability Experiment

A 5% (w/v) solution of PHB in chloroform (1.5 ml) and a 50 mM aqueous solution of cetyltrimethylammonium bromide (CTAB, 30 ml) were emulsified by 20 second ultrasonication at a frequency of 20 kHz with a power output of 200W. The emulsion was heated with stirring at 75° C. for 35 min to remove the organic solvent. The artificial amorphous PHB particles were collected by two 30 minute rounds of centrifugation at 8,000 g and 33,000 g respectively. The pellets from each round of centrifugation were resuspended in 0.25 ml $D_2O$ and combined. The concentrated granule suspension, at ca. 10% solids, was sealed in an NMR tube with a $C_6D_6$-containing glass capillary. The sample was maintained at a constant temperature of 30° C. and examined periodically by $^{13}C$—NMR. NMR spectra were recorded at 70° C. at 100.6 MHz on a Bruker AM 400 NMR spectrometer, utilising an acquisition time of 0.279 seconds, a recycle time of 5 seconds, an exponential line broadening factor of 20 Hz, and 200 transients per spectrum. Very sharp PHB resonances were observed indicating high mobility, amorphous material. The NMR line intensities, (given in Table 2 benzene peak=10.0) show no significant change over a greater than three-month period demonstrating a stable amorphous emulsion.

TABLE 2

| Time (Days) | >C=O | —OCH< | >$CH_2$ | —$CH_3$ |
|---|---|---|---|---|
| 0 | 7.5 | 7.8 | 7.7 | 13.8 |
| 32 | 7.0 | 7.5 | 7.3 | 13.0 |
| 43 | 8.0 | 8.5 | 8.1 | 14.4 |
| 74 | 7.4 | 8.2 | 7.6 | 14.3 |
| 106 | 7.9 | 8.5 | 8.2 | 14.0 |

EXAMPLE 3

Coated Film Experiment

A 5% (w/v) solution of PHB in chloroform (10 ml) and a 20 mM aqueous solution of cetyltrimethylammonium bromide (CTAB, 200 ml) were emulsified by 3 minute ultrasonication at a frequency of 20 kHz with a power output of 200W. The emulsion was heated with stirring at 75° C. for 65 minutes to remove the organic solvent. The artificial amorphous PHB particles were collected by centrifugation at 8,000 g, for 30 minutes. Surfactant coated amorphous particles were applied as a paste (ca. 1 mm thick film) to a glass X-ray slide and analysed immediately by wide-angle X-ray scattering (WAXS). The film was then allowed to dry in air at ambient temperature and analysed by WAXS after standing overnight and again after standing 36 days. After 36 days the film was heated at 125° C. for 8 hr in vacuo and then again analysed by WAXS. Values for the X-ray crystallinity of the sample are given in Table 3.

TABLE 3

| Sample | % Crystallinity (WAXS) |
|---|---|
| Undried artificial particles | 0 |
| Air-dried (O/N) artificial particles | 47 |
| Air-dried (36d) artificial particles | 57 |
| Annealed artificial particles | 73 |

The results indicate air-drying the coating has initiated crystallisation to an intermediate level of crystallinity which is then relatively stable as indicated by the 10% rise in crystallinity demonstrated by the result after 36 days. With normal injection moulded PHB develops crystallinity to 55% within a period of up to an hour post moulding and which increases to greater than 63% within a period of 10 days. The process of the present invention slows the rate of crystallisation of air-dried surfactant coated particles and they become stabilised at an intermediate level of crystallinity with the potential benefit that the polymer retains greater flexibility.

Higher levels of crystallinity can be achieved by heating the coated sample. The ability to control the crystalline state of such polymers by a series of mild treatments could have significant applications in the preparation of polymer coatings from aqueous latexes that are free of environmentally damaging solvents.

EXAMPLE 4

Density Determination for Different Polymers

Samples of particles of three polymers were made. The polymers were:
1. PHB homopolymer;
2. 50/50 mixture of PHB homopolymer and PHBV copolymer (28% HV);
3. PHBV co-polymer containing (28% HV).

The particles were prepared by taking a solution of 5% w/v of the polymer and sonicating the solution for 1 minute at 20 kHz (power output 200W) with 50 mM aqueous sodium dodecyl sulphate (30 mL) on an ice-water bath. The resulting emulsion was heated for 1 hour in a 75° C. oil bath in an open flask with stirring. The artificial particles were collected by subjecting the suspension to centrifugation at 8,0000 g for 30 minutes (20° C.) and re-centrifuging the supernatent at 33,0000 g for 45 minutes (20° C.). The pellet from each round of centrifugation was resuspended in 0.25 ml water and the two suspensions combined.

The density distributions of the artificial particles from each sample were then analysed using Nycodenz* gradients (Nycodenz*=5-(N-2,3-Dihydroxypropylacetamindo)2,4,6-triiodo-N,N'-bis(2,3-dihydroxypropyl)isophthalimide). Five solutions of aqueous Nycodenz* (30/35/40/45/50% wt/v) were layered in 25 ml aliquots into sealable ultracentrifuge tubes in order of increasing density. Artificial granule suspension (100 µl) was applied to the top of each gradient and the tubes were then sealed and laid horizontally for 45 minutes to linearise the gradients. The gradients were then centrifuged for 2 hours at 110,00 g (20°). Densities of the granule bands were determined by refractometry using the formula:

$$\rho(g/cm^3) = 3.242 n_{20°\ c} - 3.323 \text{ (at 20° C.)}$$

Results:

| Sample | | Particle Density (g/cm$^3$) |
|---|---|---|
| 1 | | 1.18 |
| 2 | | 1.17 |
| 3 | | 1.16 |
| 4 | (50 µl 1 + 50 µl 3) | 1.16, 1.18 |

In sample 2 individual particles each containing a 50/50 blend of PHB and PHBV (28% HV) gave rise to a single sharp band of intermediate density in the Nycodenz* gradient. By contrast, a simple mixture of PHB particles and PHBV (28% HV) particles (sample 4) gave rise to two sharp and easily resolvable bands corresponding to the known amorphous densities of the two polymers.

This indicates that when surfactant coated particles are prepared from mixtures of polymers of different structure and amorphous density, good mixing of the component may be achieved with a resulting particle of intermediate amorphous density.

EXAMPLE 5

Crystallisation of Surfactant Coated Particles

The crystallisation behaviour of particles made from a polymer blend was studied. A solution of chloroform containing 10 ml of 2.5% w/v PHB and 2.5% w/v PHBV (28% HV) was sonicated at 20 kHz with 20 mM aqueous cetyl trimethylammonium bromide (200 ml) for 3 minutes, power output 200W) on an ice-water bath. The resulting emulsion was transferred to a large beaker and maintained at 75° C. for 1 hour using a thermostatically controlled hot-plate. Artificial particles were collected by centrifugation at 8,000 g for 30 minutes (20° C.) and transferred to an X-ray diffraction slide. Wide angle X-ray scattering (WAXS) patterns were collected at regular intervals over a period of several hours while the sample dried in air. At the end of the last measurement (5.5 hours after sample preparation), the sample mass had decreased by 44% due to evaporation. The sample was then annealed for 100 minutes at 125° C. and the WAXS pattern again measured. Results were as follows:

TABLE 4

| Elapsed Time (min) | % Crystallisation |
|---|---|
| 0 | 0 |
| 50 | 3.6 |
| 100 | 32.5 |
| 150 | 39.2 |
| 225 | 40.9 |
| 275 | 42.0 |
| Annealed | 60.4 |

EXAMPLE 6

Preparation of Lipid Coated Amorphous Particles

Artificial particles coated with lipid were prepared by replacement of the surfactant coating of surfactant coated particles using detergent-micellized phospholipids. Soy phosphatidyl-choline (Sigma P5638, type II-S containing 10–20% phosphatidyl-choline, the remainder being other phospholipids) was purified by the method of Eytan, G. D., "Reconstitution of Membrane Function with Liposomes", in Techniques in the Life Sciences, vol B416 (Elsevier Biomedical, 1982) and stored at −20° C. as a chloroform solution at ca. 333 mg/ml (0.1 mg/ml BHT preservative). A 2.4 ml portion of this solution was evaporated in a heavy-walled glass test tube using a stream of dry nitrogen. Diethyl ether (5 ml) was added and the sample was again dried with nitrogen. The lipids were then dried in a vacuum for several hours, yielding 767 mg of a yellow gum. A solution of sodium cholate (2% w/v) in a buffer of 50 mM sodium phosphate (pH8.0) was made up and 18.4 ml were added to the gum. The sample was sonicated at 20 kHz, (power output 50W), for 5 minutes on an ice water bath. The product was a clear yellow homogeneous suspension containing 40 mg/l soy lipids.

Artificial particles were prepared by the general method using sodium cholate as the surfactant. A 5% w/v solution of PHB in chloroform (20 ml) was sonicated at 20 kHz with 50 mM aqueous sodium cholate (200 ml) (power output 200W) for 3 minutes on an ice-water bath. The procedure was repeated once to give a total of 440 ml of emulsion, which was transferred to a large beaker and maintained at 75° C. for 1 hour using a thermostatically controlled hot-plate. Nine 20 ml portions of the resulting artificial particles suspension were taken and centrifuged to collect the particles. Each sample was centrifuged first at 8,000 g for 30 minutes (20° C.) and then re-centrifuged at 33,000 g for 45 minutes (20° C.). Pellets from sample 1 (the control) were resuspended in $D_2O$ (0.25 ml each), combined and reserved.

The pellets from the two centrifugations for each of the remaining samples were resuspended in a buffer containing soy lipid suspension diluted with varying amounts of sodium cholate (2% w/v) in buffer (50 mM sodium phosphate, pH 8.0). The two resuspended pellets were combined for each sample, giving 0.5 ml samples, which were then dialysed to remove the surfactant. The samples were transferred to cellulose dialysis bags and dialysed exhaustively at room temperature against buffer (50 mM sodium phosphate, pH 8.0) containing 25 g/l Amberlite XAD-2 resin. $^{13}$C-NMR spectra were obtained for all samples at 70° C. using a $d_8$-benzene capillary as internal reference (conditions as previously described). The percentage of the amorphous particles protected by the addition of soy lipid was estimated by comparing the intensities of the methyl resonances in the NMR spectra with that of the control sample. The results are given in Table 5.

TABLE 5

| Sample | Lipid in Resuspension Buffer (mg/ml) | % Particles protected from Denaturation by dialysis |
|---|---|---|
| 1 | 40 | 81 |
| 2 | 30 | 76 |
| 3 | 20 | 84 |
| 4 | 10 | 82 |
| 5 | 4 | 0 |
| 6 | 2 | 0 |
| 7 | 1 | 0 |
| 8 | 0 | 0 |

EXAMPLE 7

Preparation of Artificial Particles by Bulk Preparation Method 150 ml of pre-peroxide material prepared by method of EP-145 233 was placed in each of two 250 ml conical flasks. 1.5 g of Synperonic* A50 was added to one of the flasks. The flasks were then placed in a shaking water bath at 80° C. and agitated. The flasks were allowed to reach the temperature of the water bath and the pH was adjusted to 7.0 with ammonium hydroxide (18% solution). 9.0 ml of 106.5 vol hydrogen peroxide was added to each flask. The flasks were left in the water bath for 10 hours during which time the pH was maintained by the periodic addition of further ammonium hydroxide (18% solution). Once the reaction was completed the samples were cooled and an analysis conducted. The particle size was measured by a Malvern Master Sizer MS20, the particle density was measured using CsCl density gradient. Analar CsCl (available from BDH) was used to prepare CsCl solutions in de-ionised water containing 15, 20, 25 and 28% w/w CsCl. 2 ml of each CsCl solution was placed in a centrifuge tube in order of increasing density using a pasteur pipette. In this method the solutions must not be disturbed as the following solution is added. A few drops of the sample suspension was added to the top of the prepared gradient using a pasteur pipette. The gradients were spun at 4000 rpm for 10 minutes.

Flask 1 - with surfactant

| | |
|---|---|
| particle size (d50 μm) | = 0.98 |
| particle density | = 60% at 1.176 g/ml |
| | 30% at 1.231 g/ml |
| | 10% between the bands |

Flask 2 - no surfactant

| | |
|---|---|
| particle size (d50 μm) | = 9.96 |
| particle density | = 0% at 1.176 g/ml |
| | 100% at 1.231 g/ml |

In the absence of surfactant, as the peroxide removes the impurities from the particle surface, extensive flocculation occurs. This is associated with an increase in particle density resulting from complete crystallisation of the particles. In the presence of surfactant flocculation is completely removed, the particles staying in their monodisperse size of 1 μm and hence remain largely amorphous as assessed by the lower density of the particles.

This example was repeated with the following surfactants and very similar results were obtained: Synperonic* A7, Synperonic* A11, Synperonic* A20, Synperonic* 91AT (all available from ICI), Berol 08 (available from Berol), Genepol T-500 (available from Hoechst), Synperonic* PE/F88, Synperonic* PE/F108, Synperonic* NP30 (available from ICI), PE 6800 (available from BASF), Atlas G2541 (available from ICI).

We claim:

1. A polymer composition in the form of an aqueous latex or a flowable powder of individual particles or loose agglomerates, substantially free of cellular protein and comprising a crystallisable biodegradable polyhydroxyalkanoate capable of forming over 30% crystallinity in the form of particles having a largest dimension in the range 0.1 to 5 μm and having on their surface a phospholipid or a surfactant, said polymer having a molecular weight $m_w$ of over 50000 and having a crystallisation half life of more than 0.1 day at ambient temperature.

2. A polymer composition according to claim 1 wherein the surfactant or phospholipid covers 50% or more of the surface of the particles.

3. A polymer composition according to claim 1 wherein the polymer is polyhydroxybutyrate or polyhydroxybutyrate-co-valerate co-polymer.

4. A polymer composition according to claim 1 in which the surfactant is non-ionic and chosen from $C_{9-20}$ alkylethoxylates, aromatic ethoxylates and block copolymers of ethylene oxide and propylene oxide.

5. A process for the preparation of a polymer composition according to claim 1 by lysing microorganism cells containing the polymer and removing non-polymer cell material from the surface of the polymer using an oxidising agent in the presence of a surfactant or phospholipid.

6. A process according to claim 5 wherein non-polymer cell material is separated from the polymer using a proteolytic enzyme and/or a surfactant prior to treating the polymer with an oxidising agent in the presence of a surfactant or phospholipid.

7. A process of making a polymer composition according to claim 1 by the steps of:
    (a) dissolving the polymer in a solvent of low solubility in water;
    (b) emulsifying the resulting solution in an aqueous solution of a surfactant or phospholipid; and
    (c) removing solvent from the resulting emulsion disperse phase.

8. A process according to claim 7 in which the solvent is a volatile compound and step (c) is effected by contacting the emulsion with an aqueous solution of at least one amphipathic agent in a content of at least its critical micelle concentration.

9. A process according to claim 8 in which contacting is through a membrane made of cellulose and having a molecular weight cutoff in the range 10000–20000 Da.

10. A process according to claim 8 in which the compound boils at not over 85° C. at atmospheric pressure and is a hydrocarbon or halogenated hydrocarbon.

11. A process of making a polymer structure by confining particles as defined in claim 1 and causing mutual adhesion and/or crystallisation thereof.

* * * * *